US00RE43364E

(19) United States
(12) Reissued Patent
Marshall

(10) Patent Number: US RE43,364 E
(45) Date of Reissued Patent: May 8, 2012

(54) METHOD AND APPARATUS USING A SCANNED IMAGE FOR MARKING BRACKET LOCATIONS

(75) Inventor: Michael Craig Marshall, Prior Lake, MN (US)

(73) Assignee: GeoDigm Corporation, Chanhassen, MN (US)

(21) Appl. No.: 12/730,484

(22) Filed: Mar. 24, 2010

Related U.S. Patent Documents

Reissue of:
(64) Patent No.: 7,347,686
Issued: Mar. 25, 2008
Appl. No.: 10/349,559
Filed: Jan. 22, 2003

U.S. Applications:
(60) Provisional application No. 60/351,311, filed on Jan. 22, 2002.

(51) Int. Cl.
*A61C 5/00* (2006.01)
(52) U.S. Cl. ..... 433/3
(58) Field of Classification Search ..... 433/3, 24
See application file for complete search history.

(56) References Cited

U.S. PATENT DOCUMENTS

| | | | |
|---|---|---|---|
| 4,575,805 | A | 3/1986 | Moermann et al. |
| 4,611,288 | A | 9/1986 | Duret et al. |
| 4,837,732 | A | 6/1989 | Brandestini et al. |
| 5,113,424 | A | 5/1992 | Burdea et al. |
| 5,267,293 | A | 11/1993 | Virta |
| 5,273,429 | A | 12/1993 | Rekow et al. |
| 5,343,391 | A | 8/1994 | Mushabac |
| 5,347,454 | A | 9/1994 | Mushabac |
| 5,368,478 | A | 11/1994 | Andreiko et al. |
| 5,372,502 | A | 12/1994 | Massen et al. |
| 5,416,822 | A | 5/1995 | Kunik |
| 5,431,562 | A | 7/1995 | Andreiko et al. |
| 5,448,472 | A | 9/1995 | Mushabac |
| 5,518,397 | A | 5/1996 | Andreiko et al. |
| 5,533,895 | A | 7/1996 | Andreiko et al. |
| 5,549,476 | A | 8/1996 | Stern |
| 5,569,578 | A | 10/1996 | Mushabac |
| 5,588,430 | A | 12/1996 | Bova et al. |
| 5,605,459 | A | 2/1997 | Kuroda et al. |
| 5,879,158 | A | 3/1999 | Doyle et al. |
| 6,068,482 | A | 5/2000 | Snow |
| 6,123,544 | A | 9/2000 | Cleary |
| 6,143,003 | A | 11/2000 | Cosman |

(Continued)

OTHER PUBLICATIONS

Hayashi, T. et al. "A Computerized System for Analyzing Occlusal Relations During Mandibular Movements," *The Intl. Journal of Prosthodontics*, vol. 7, No. 2, pp. 108-114 (Mar./Apr. 1994).

*Primary Examiner* — Ralph A Lewis
(74) *Attorney, Agent, or Firm* — Merchant & Gould P.C.

(57) ABSTRACT

Locating the physical placement location of a plurality of brackets on a patient's study cast includes obtaining an array of data points from a study cast and generating a virtual model of a dental impression from the array of scanned data points, Individual teeth from the dental impression can be manually severed or "cut" and manually dragged from a start position to a finished position to determine a treatment plan. The orthodontist virtually marks the position on the virtual model where a physical bracket is desired. A marking device physically marks a physical model with the corresponding bracket locations. The physical model can serve as a template or guide to locate brackets for an indirect bonding style tray.

14 Claims, 14 Drawing Sheets

U.S. PATENT DOCUMENTS

| | | | |
|---|---|---|---|
| 6,322,359 | B1 | 11/2001 | Jordan et al. |
| 6,371,761 | B1 | 4/2002 | Cheang et al. |
| 6,409,504 | B1 | 6/2002 | Jones et al. |
| 6,450,807 | B1 | 9/2002 | Chishti et al. |
| 6,554,613 | B1 | 4/2003 | Sachdeva et al. |
| 6,632,089 | B2 | 10/2003 | Rubbert et al. |
| 6,648,640 | B2 | 11/2003 | Rubbert et al. |
| 6,688,886 | B2 | 2/2004 | Hughes et al. |
| 6,905,337 | B1 | 6/2005 | Sachdeva |
| 7,214,056 | B2 | 5/2007 | Stockstill |
| 7,347,686 | B2 | 3/2008 | Marshall |
| 7,387,511 | B2 | 6/2008 | Marshall |
| 2003/0224316 | A1 | 12/2003 | Marshall |
| 2004/0029078 | A1 | 2/2004 | Marshall |
| 2004/0066877 | A1 | 4/2004 | Arai et al. |
| 2005/0239013 | A1 | 10/2005 | Sachdeva |

[X, Y, Z, 1]

[X', Y', Z', 1]

METHOD AND APPARATUS USING A SCANNED IMAGE FOR MARKING BRACKET LOCATIONS

Matter enclosed in heavy brackets [ ] appears in the original patent but forms no part of this reissue specification; matter printed in italics indicates the additions made by reissue.

*CROSS REFERENCE TO RELATED APPLICATIONS*

*This application claims priority to U.S. Provisional Application Ser. No. 60/351,311, filed Jan. 22, 2002, and titled Method and Apparatus Using a Scanned Image for Marking Bracket Locations.*

TECHNICAL FIELD

The invention relates generally to a method and apparatus for locating brackets to be placed on patients' teeth via indirect bonding; more particularly to a system, method and apparatus for automatically marking located bracket positions on a study cast subsequent to electronically determining the bracket locations on a scanned image of the teeth; and more particularly still an image driven system for manipulating the scanned image of teeth to a final position, electronically marking the placement of brackets in the finished position, and automatically marking a study cast with the selected electronic positions.

BACKGROUND

Dental study casts are an integral part of a dentist's understanding of how a patient's teeth and bite function in a static relationship. This static relationship serves three important functions. The primary function is one of a diagnostic function for interpretation of any discrepancies or problems that exist within the bite relationship. The second function is educational. For example, the study casts provide better communication as a concrete model while helping the patient understand any discrepancies that may exist in the way their teeth function in that static relationship. Third, the dental study casts serve an important medical/legal function in defining the pre-existing static bite relationship prior to the performance of any work. This work can be defined either from an oral surgical standpoint, prosthetic standpoint or orthodontic/periodontal standpoint.

Yet another function is to provide a model when creating orthodontic devices. In the prior art, impressions are taken of the patient's teeth with a study cast or model taken from the impression. It is also known that either the impression and/or study cast can be electronically digitized. For example, U.S. Pat. No. 6,217,334, commonly assigned to the assignee of the present application describes a scanning process. U.S. Pat. No. 6,217,334 is hereby incorporated herein by reference and made a part hereof. By digitizing the model, a set of electronic data of the patient's teeth and surrounding soft tissue is created which can be electronically manipulated, displayed, stored and transmitted.

Bonding brackets to teeth for the purpose of orthodontic treatment is known. One method of securing the brackets to the teeth comprises manually locating the brackets by hand. Another method involves manually placing the brackets on a model of the patient's teeth, transferring the brackets to a tray and transferring the brackets from the tray to the correct location on the patient's teeth. This latter method is commonly known as indirect bonding. While indirect bonding generally provides an accurate location of the brackets, it does not take advantage of advances in the electronic imaging of teeth.

Therefore, there arises a need in the art to provide a system for providing a scanned image set of data of a patient's teeth, displaying the scanned image set to generate a virtual model, storing the finish positions of the virtual model teeth after manipulation of the teeth into a final desired position, storing electronically generated bracket marker points on the teeth of the virtual model (e.g., where the physical brackets may be placed in order to move the physical teeth into a final, desired position), and automatically marking the physical location of the marker points on a model, wherein an indirect bonding tray can be created. The present invention directly addresses and overcomes the shortcomings of the prior art.

SUMMARY

The present invention provides for an imaging and marking system for locating the physical placement location of a plurality of brackets on a patient's study cast. In one preferred embodiment of the present invention, the system may include a three-dimensional scanner; a computer including a processor, memory associated with the processor, one or more input devices, and a video display unit; and a marking device.

The scanner functions to gather an array of data points from the impression and/or study cast. The computer generates a virtual model of from the array of scanned data points. The marking device takes the locations identified by the orthodontist from the virtual model and transfers the data to the physical model.

After the array of data points is collected and the computer generates an image of a virtual model, the virtual model is displayed on the video display unit for the orthodontist, dentist or other medical professional (hereafter collectively referred to as "orthodontist") to review. Each tooth that is desired to be moved by the orthodontist in an orthodontic treatment plan may be manually severed or "cut" from the other portions of the virtual model. Accordingly, the virtual model becomes segmented into a plurality of virtual model teeth, each of which may be manually dragged with a computer input device by the orthodontist from a starting position (e.g., that position where the tooth originally begins) to a finished position (e.g., the position that the tooth will be physically located at the end of the treatment plan). The computer stores the beginning and ending vectors of each manipulated teeth.

When each of the desired teeth have been manipulated into the desired finished locations, the orthodontist points and clicks with a marking tool on the position of the tooth where a physical bracket may be located to induce the necessary forces on the tooth to move the physical tooth from the starting position to the finished position. This point is also stored in memory by the computer. The computer then determines the starting positions of the plurality of teeth and may display the same. An output file of the bracket marker locations is transmitted to the marking device.

The marking device takes the output file and physically marks a physical model with the bracket location information. The marking device may take the form of a pen or other device which provides visually perceptible indicia of the bracket placement. The marker device may constitute a robotic arm which moves about the fixed model marking the known coordinates from the output file. Alternatively, the marker device may have a fixed marking device and move the model into engagement with the marking device or both the marking device and the model may move into engagement with one another.

Subsequent to the marking operation, the model can serve as a template or guide to locate brackets for an indirect bonding style tray. In this manner, the placement of brackets is improved.

According to one aspect of the invention, there is provided a computer implemented method of automatic marking of locations on a study cast for creation of an indirect bonding tray, the method comprising: displaying an electronic model image corresponding to the actual study cast of a patient with the individual teeth in starting positions; storing an array of start coordinates for the individual teeth; storing an array of finish coordinates once the teeth are moved to finish locations; storing an array of bracket mark locations for one or more individual teeth with respect to the finish locations; and calculating the bracket mark locations in connection with the start locations based on the stored start and finish coordinates, wherein the bracket mark locations can be viewed with the teeth in the start locations.

According to another aspect of the invention, there is provided a method as recited in the preceding paragraph and further comprising the step of generating an output file with the bracket mark locations in connection with the start locations and transmitting the output file to a marking device for marking a study cast with the bracket mark locations. According to yet another aspect, there is provided the foregoing method further comprising the step of manually cutting the teeth into individual teeth from the electronic model image.

Accordingly to yet another aspect of the invention, there is provided a system for marking of locations on a study cast for creation of an indirect bonding tray, the apparatus comprising: means for displaying an electronic model image corresponding to the actual study cast of a patient with the individual teeth in starting positions; means for storing an array of start coordinates for the individual teeth; means for storing an array of finish coordinates once the teeth are moved to finish locations; means for storing an array of bracket mark locations for one or more individual teeth with respect to the finish locations; and means for calculating the bracket mark locations in connection with the start locations based on the stored start and finish coordinates, wherein the bracket mark locations can be viewed with the teeth in the start locations.

Another feature of the present invention is the optional automation of the cutting function between the teeth of interest. In this embodiment, the system constructed in accordance with the principles of the present invention includes a computing system that is programmed for automatically determining the location of individual teeth within an electronic model image of a patient's mouth to allow the manipulation of the electronic model images by end users. The method and apparatus determines possible horizontal cut lines within a horizontal plane cut through the electronic model image corresponding to possible separation lines between teeth, determines possible vertical cut lines within a vertical plane cut through the electronic model image corresponding to possible separation lines between teeth, and automatically determines the locations of individual teeth using the possible horizontal cut lines and the possible vertical cut lines.

While the invention will be described with respect to a preferred embodiment configuration and with respect to particular devices used therein, it will be understood that the invention is not to be construed as limited in any manner by either such configuration or components described herein. Also, while the particular types of scanning devices, input devices, and marking device used in the preferred embodiment are described herein, it will be understood that such particular components are not to be construed in a limiting manner. Instead, the functionality of those devices should be appreciated. Further, while the preferred embodiment of the invention will be described in relation to cutting and moving teeth in a digitized image in order to locate brackets for use in orthodontic treatments, it will be understood that the scope of the invention is not to be so limited. The principles of the invention apply to the use of cutting, moving and marking a digitized image for later use in a physical model. These and other variations of the invention will become apparent to those skilled in the art upon a more detailed description of the invention.

The advantages and features which characterize the invention are pointed out with particularity in the claims annexed hereto and forming a part hereof. For a better understanding of the invention, however, reference should be had to the drawing which forms a part hereof and to the accompanying descriptive matter, in which there is illustrated and described a preferred embodiment of the invention.

BRIEF DESCRIPTION OF THE DRAWINGS

Referring to the drawing, wherein like numerals represent like parts throughout the several views.

DETAILED DESCRIPTION

Although the present invention will be described with respect to digitizing the model, it should be appreciated that the principles of the present invention may be applied to a digitized impression. In the latter case, a computer can invert the scanned impression to provide a positive image of the patient's teeth.

Figure 1:
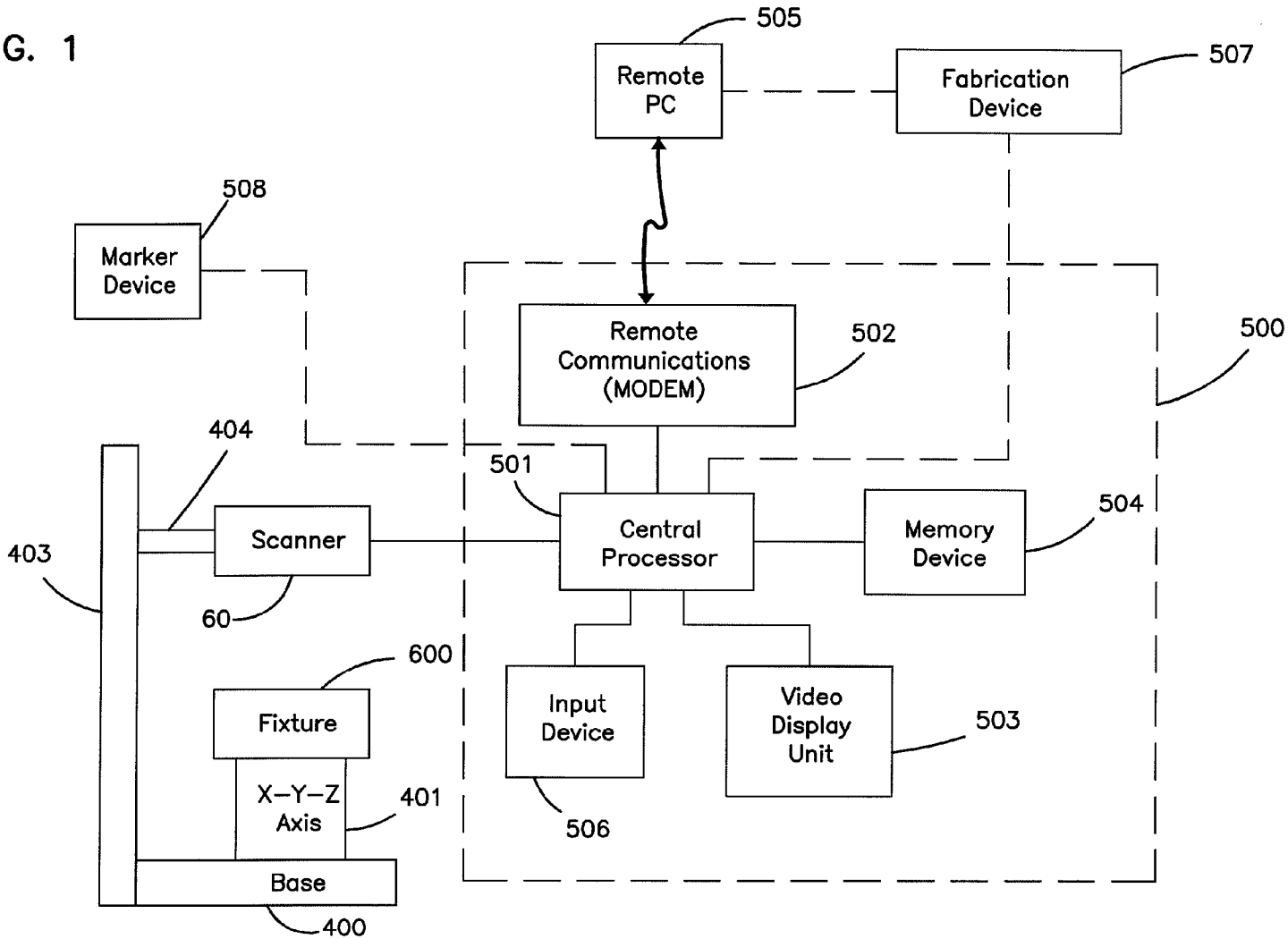
FIG. 1 is a schematic functional block diagram of the various components of a system constructed in accordance with the principles of the present invention.
Figure 2:
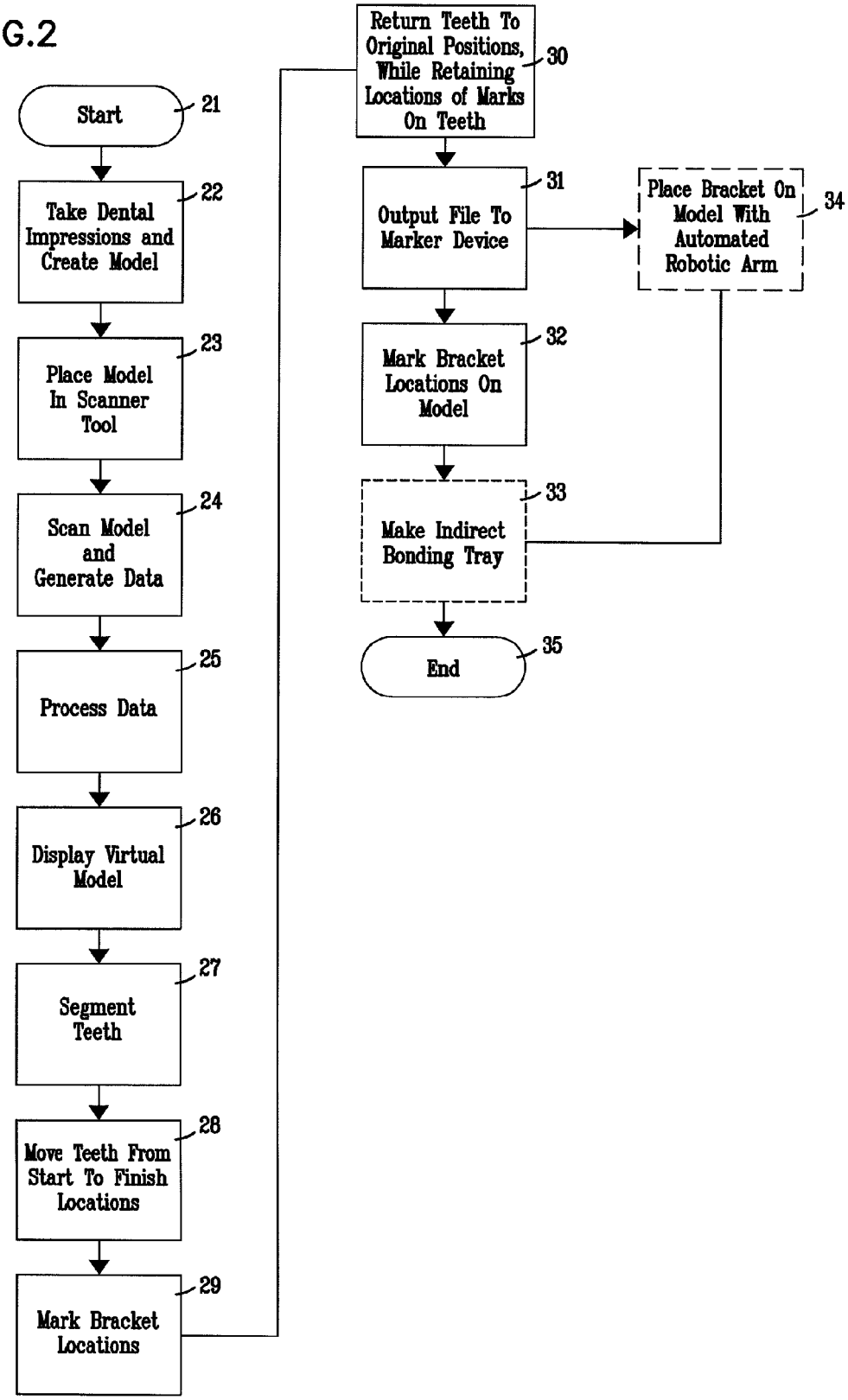
FIG. 2 is a logic flow diagram of the various steps utilized in connection with the system of the present invention.

Referring first to FIGS. 1 and 2, the overall method of the present invention is illustrated generally by the designation 20 and starts at 21. First, at block 22, a dental impression of a patient's teeth and surrounding soft tissues (hereafter referred to collectively as "teeth" for convenience) is taken. The impression material hardens, forming a negative image of the teeth. Generally lower and upper trays are used in connection with taking the impression. Such trays are well known in the art and trays which may be used in connection with scanning an impression are described in U.S. Pat. No. 6,217,334 identified above. A bite/clutch tray is used in connection with determining the correct spatial orientation and relationship between the upper and lower impressions. A study cast is then formed from the impression. The forming of the study cast is well known in the art.

At block 23, the study cast is placed in the tool or fixture 600 (best seen in FIG. 1). The fixture 600 is used to securely hold the study cast during the scanning step. The fixture 600 may also aid the scanning step by helping rotate the mold so that the image data can be properly generated.

Next at block 24, the scan of the study cast occurs. In the preferred embodiment, a dental scanner manufactured by Geodigm Corporation of Minneapolis, Minn. may be used. The operation and scanning methodology used by this type of line scanner is generally described in U.S. Pat. No. 6,217,334.

At block 25 the image data is processed by processor 501. Such processing may include generating an image for display at block 26 on a video display unit 503; converting the image scan data into CNC or other format of output for use by a fabrication device 507 (also known as a prototyping apparatus); storing the image scan data in a memory location or device 504; and/or transmitting the negative image scan data to a remote processor 505 via modem block 502.

In the preferred embodiment, a software package which may be used to generate three dimensional images from the line scan data is the package under the designation "e-Modeler" by the assignee hereof, Geodigm Corporation. Other scanning packages such as the DataSculpt software available from Laser Design Inc. of Minneapolis, Minn. might also be used.

At block 27, the orthodontist manually segments the teeth in the virtual model with a CAD/CAM type "cutting" utility. This is typically accomplished with a pointing tool (e.g., a mouse, trackball, pointing pen, touch pad, touch sensitive screen, etc.) or other input device 506 by clicking on the point and dragging a line to initiate the cutting function. The function may also be implemented in two dimensions the same general manner by drawing a rectangle around the portion of the image which is intended to be segmented (best seen in FIG. 4b at 64). The orthodontist continues making cuts around each of the teeth which are desired to be moved in the virtual image. It will be appreciated that the segmented virtual image teeth will generally correspond to the physical teeth in an orthodontic treatment plan on a patient.

Figure 3A:
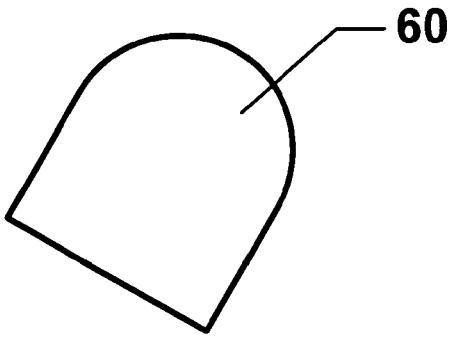
FIGS. 3a, 3b, and 3c illustrates the array data stored in connection with each of the teeth which are cut from the electronic model image.
Figure 3B:
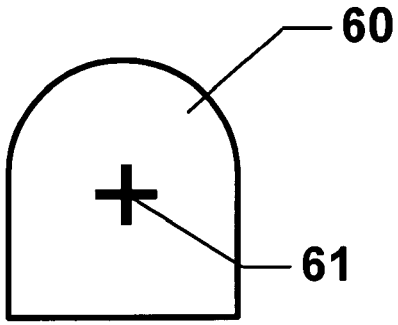
Figure 3C:
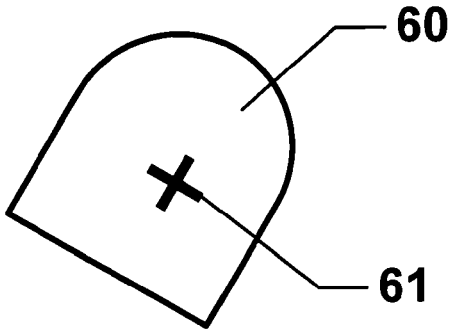

At block 28, the operator moves each of the now segmented teeth from their start positions to their final positions. The orthodontist then marks the desired locations of brackets on the virtual teeth with the input device 506. The processor 501 stores the original position data of a tooth 60 in its start position (best seen in FIG. 3a) in an [XY Z 1] array in memory device 504. The finish position data of tooth 60 in its finish position (best seen in FIG. 3b) is stored by the processor 501 in an [X'Y'Z' 1] second array in memory device 504.

Figure 3D:
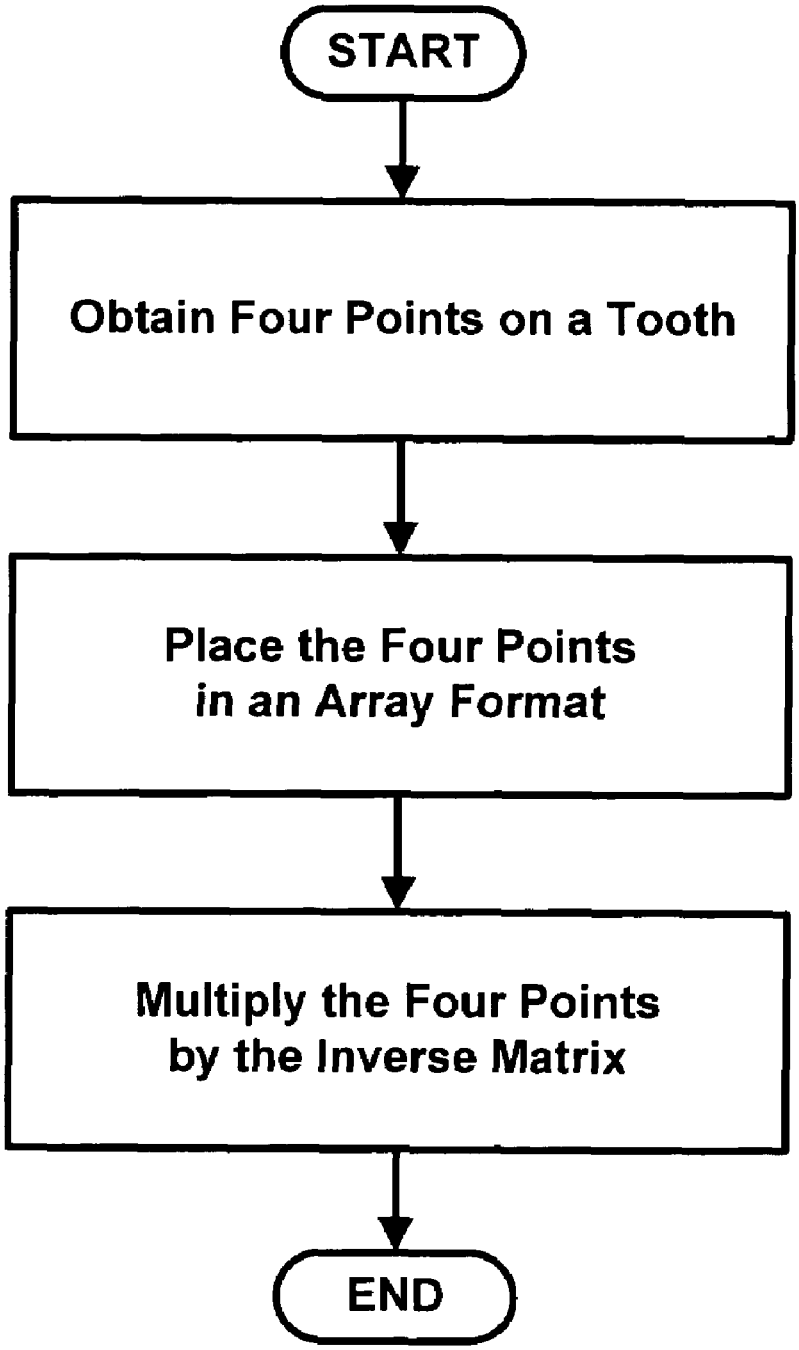
FIG. 3D illustrates an operation flow to determine bracket marker locations on an occluded state tooth.

The moved individual teeth 60 are then marked at block 29. The mark is designated by 61 (best seen in FIGS. 3b, 3c, 4d and 4e) by locating four points on the tooth. These data points are also stored. The processor maintains the position of the markers on the virtual teeth 60 by storing the data points. The markers can be repositioned on the teeth 60 by tracking changes to the stored arrays. For example, the location of the bracket markers can be determined on the starting position of the teeth (as shown in FIG. 3D) by multiplying the points by the inverse matrix.

At block 30, the teeth are returned to the original start positions by the processor 501, while retaining the desired location of the markers 61 on the marked teeth 60. At block 31, an output file is generated to provide the coordinate data of the marks. At block 34, the data may optionally be provided to an automated robotic arm to place the brackets onto the model. However, proceeding to block 32, the marker device 508 operates to create visually perceptible indicia on the physical model where the brackets should be located.

At block 33, a lab can create an indirect bonding tray. The process ends at 35.

Referring more specifically to FIG. 1, the functional blocks of the electronic components of the present invention are illustrated. The components include a computer 500 which preferably includes a processor 501, a video display unit 503, a memory device 504, a user input device 506 (e.g., a mouse, trackball, touch pad, touch screen and/or keypad, etc.), and a modem 502. Also illustrated is a remote computer 505, a fabrication device 507, and the scanner 60 (and its attendant X-Y-Z axis controllers and motors).

It will be appreciated by those of skill in the art that the computer 500 may be a personal computer (e.g., a Pentium based PC) or a special purpose computer. Further, the video display unit 503 may include any number of display devices such as cathode ray tubes, LCD displays, etc. Still further, the memory device 504 may include hard drives, floppy drives, magnetic tape, CD-ROM, random access memory, and read-only memory devices. Further, the modem 502 is illustrated to show a communications capability. Such capability may also be by way of a network, etc.

As discussed above, marker device 508 takes the output file and physically marks a physical model with the bracket location information. The marking device may take the form of a pen or other device which provides visually perceptible indicia of the bracket placement. The marker device may constitute a robotic arm which moves about the fixed model marking the known coordinates from the output file. Alternatively, the marker device may have a fixed marking device and move the model into engagement with the marking device or both the marking device and the model may move into engagement with one another. In the preferred embodiment, the scanner 60 may be used as the marker device 508 by locating a pen on the scanner head.

Fabrication device 507 may be connected directly to the computer 500 or may be connected to a remote computer 505. The fabrication device 507 may be any number of devices which can utilize computer generated data and create a three-dimensional object from such data. One example of such a machine are the devices utilizing stereo lithography technology manufactured by 3-D Systems of Valencia, Calif. under the model designations SLA-250 and SLA-500. Another example is the device utilizing filament technology (fused deposition modeling) manufactured by Statasys Corporation of Minneapolis, Minn. under the model designation FDM-1500.

In operation the scan data is generated by the scanner 60 and provided to the processor 501. The scan data may be saved in a memory device 504 as a permanent record of the baseline condition of the patient's teeth, or temporarily prior to one of several other options. The data may be transmitted to a remote PC 505 for storage, study by a consulting dentist (or physician), or fabrication of a study cast by fabrication device 507. The fabrication device 507 may optionally be connected directly to computer 500. These and other options may be selected by the computer 500 user via the input device 506.

The programming operation of the processor 501 preferably provides for scanning each of the upper and lower models and the bite registration impression. These scans provide the information necessary to create an electronic equivalent of the physical study casts.

Figure 4A:
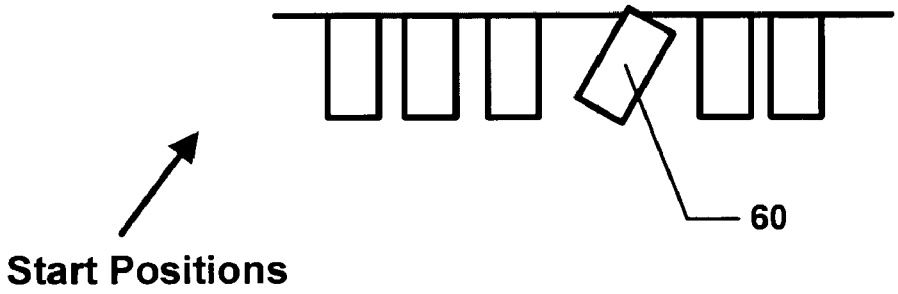
FIG. 4a schematically illustrates a portion of an electronic model image prior to moving individual teeth.
Figure 4B:
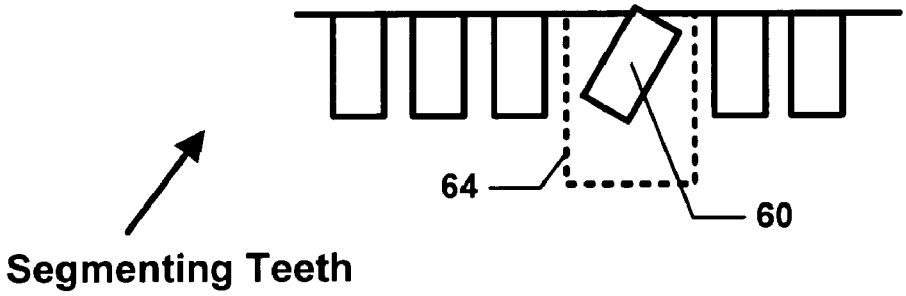
FIG. 4b schematically illustrates the electronic model image of FIG. 3a in which a single tooth has been identified for cutting from the other portions of the electronic model image.
Figure 4C:
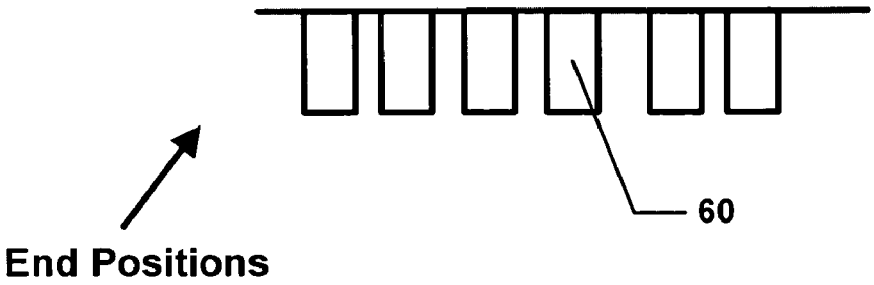
FIG. 4c schematically illustrates the electronic model image of FIG. 3b in which the teeth have been moved to the finished locations.

Referring to FIGS. 4a-4e, several schematic representations of several teeth of the virtual image model are shown. FIG. 4a illustrates the teeth in their start position. While several teeth are shown, only tooth 60 is designated for clarity throughout FIGS. 4a-4e. FIG. 4b illustrates the segmenting process of tooth 60 from the other adjacent teeth in order to move tooth 60. The dotted line 64 illustrates the segmenting or cutting tool function. Assuming that each of the teeth will be moved to accomplish the finish positions shown in FIG. 4c, the orthodontist would use the segmenting or cutting tool on each of the teeth. However, it will be appreciated that only one or more teeth might be segmented for movement.

As noted above, one manner in which the teeth may be manipulated is to virtually cut between the teeth by drawing a "cut" line between the teeth which should be separated. It will be appreciated that this is accomplished by pointing and clicking using a separate tool in a cad/cam type library. By using these types of tools, the objects are released from their static relationship to other objects and the released object may be moved. Other manners of segmenting the teeth will be described in the alternative embodiment described below.

Figure 4D:
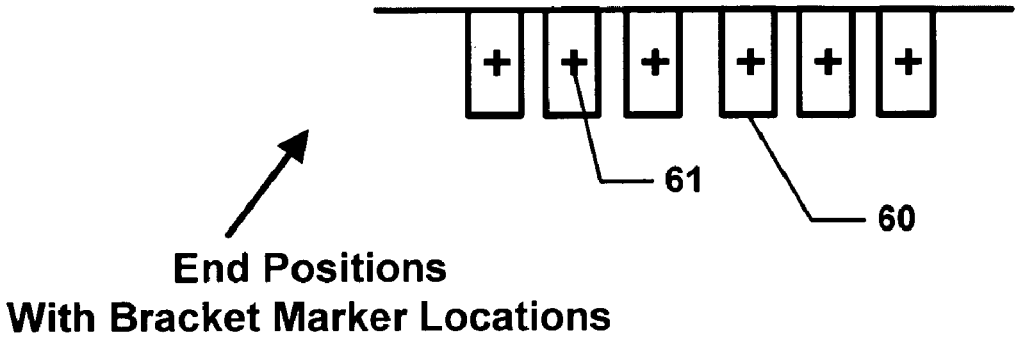
FIG. 4d schematically illustrates the electronic model image of FIG. 3c in which the bracket locations have been identified and marked on the teeth in their respective finished locations.
Figure 4E:
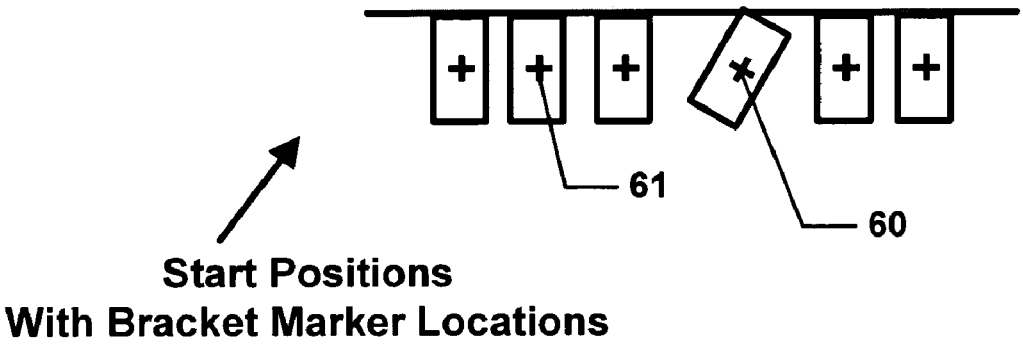
FIG. 4e schematically illustrates the electronic model image of FIG. 3d in which the teeth have been returned to the start positions while retaining the bracket location marking.

At FIG. 4d, the teeth in their finish positions are marked, while at FIG. 4e, the teeth are returned to their start positions with the bracket markers remaining in the spots on the teeth which were selected in the finish or end positions.

Alternative Embodiment

An alternative manner in which the teeth may be manipulated is next described. In this embodiment, there is provided a system, method and article of manufacture for automatic determination of the location of individual teeth within an electronic model image of a patient's mouth to allow the manipulation of the electronic model images by end users.

Figure 5A:
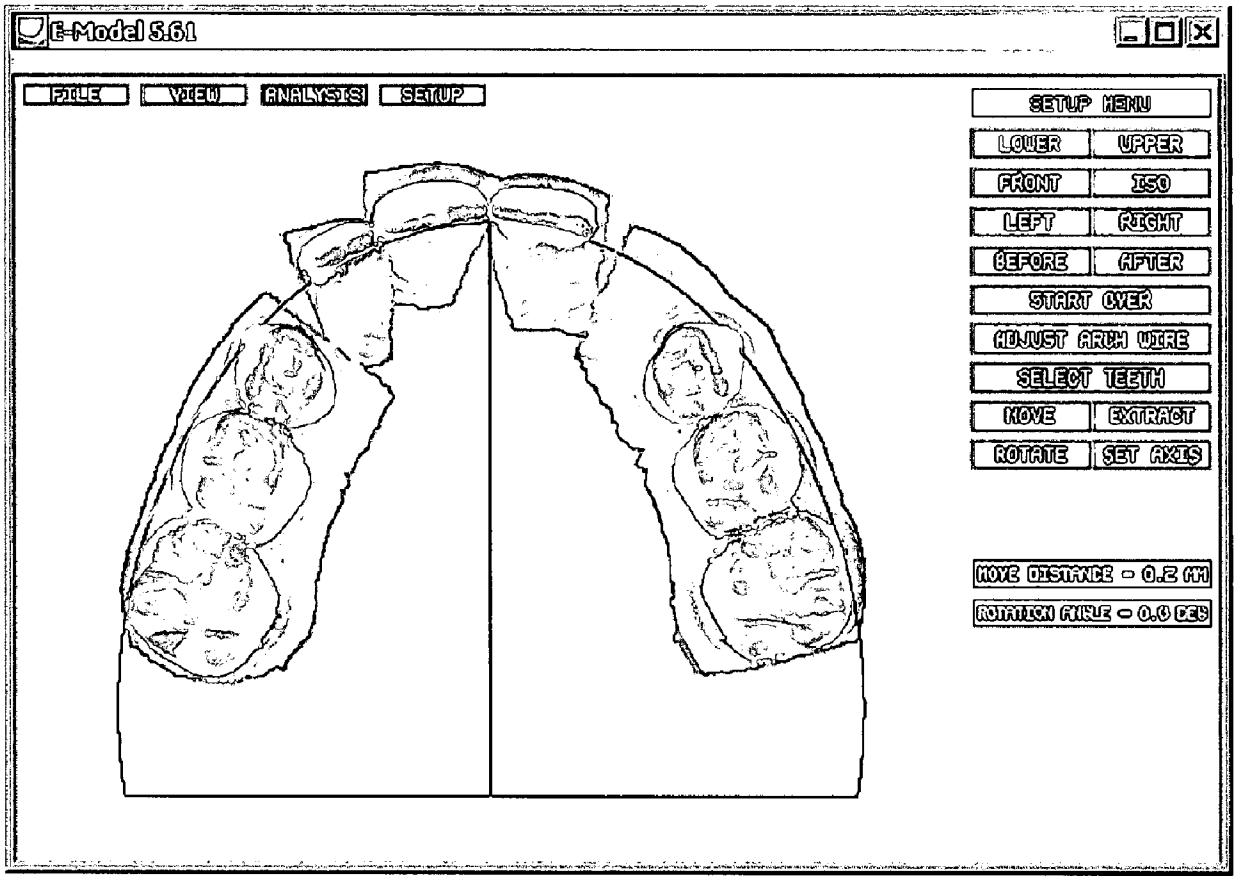
FIG. 5a illustrates an electronic model image of a patient's mouth in which individual teeth have been identified and moved locations in support of a plan of treatment according to one embodiment of the present invention.

FIG. 5a illustrates an electronic model image of a patient's mouth in which individual teeth have been identified and moved locations in support of a plan of treatment according to one embodiment of the present invention. An electronic model of a patent's upper teeth are shown 101 in which individual teeth 111-113 have been electronically moved to allow a dental practitioner to visualize the treatment plan. In order for this process to occur, two events must occur. First, an electronic model for the teeth must be generated. This occurs when a physical mold or impression of the mouth is generated. This impression is then electronically scanned to generate the model.

Once the electronic model has been generated for the impression, the locations of the individual teeth need to be determined. This location identification may occur using manually specified locations entered into a computing system by a user. Alternatively, these locations may be automatically determined using information contained within the electronic model. Once the locations of the teeth are known, the electronic model may be cut into a set of individual teeth images 111-113 that may be manipulated on a computer display device.

Figure 5B:
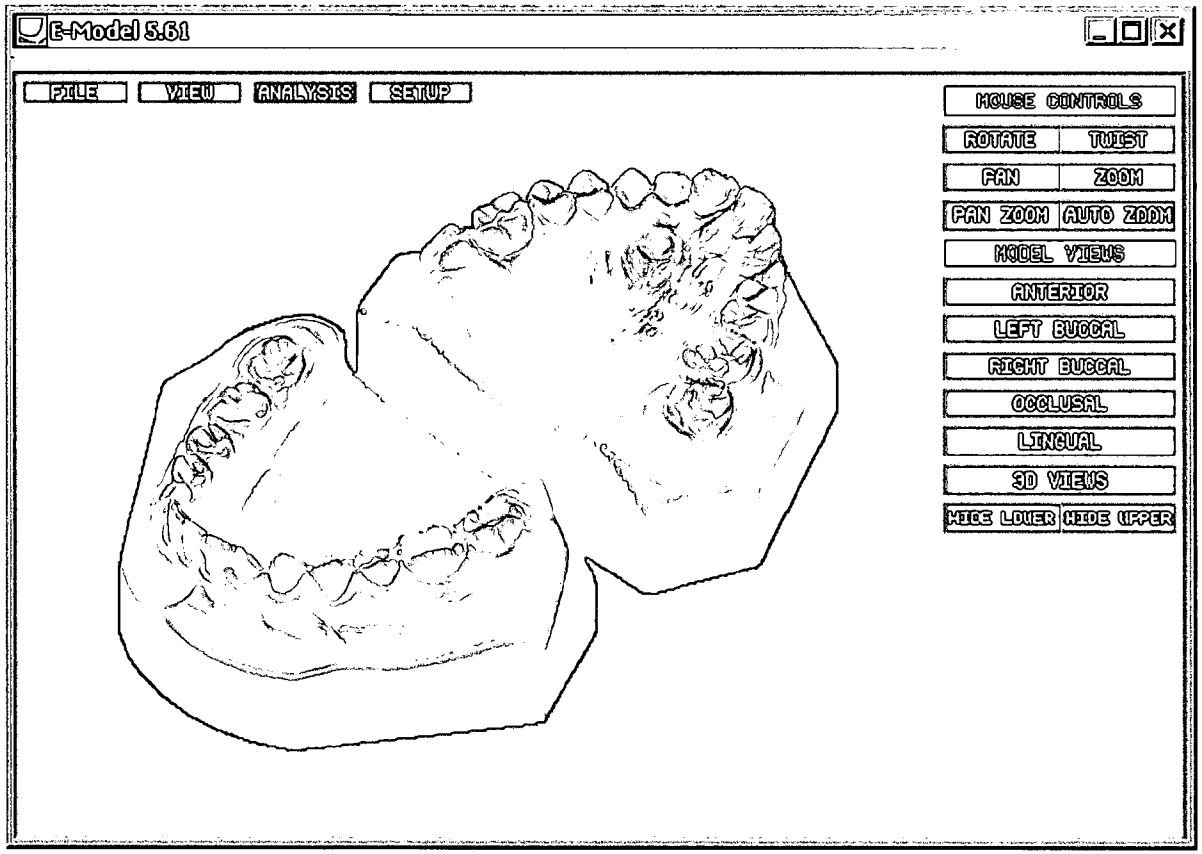
FIG. 5b illustrates an electronic model image of a patient's mouth useful for implementing an embodiment of the present invention.

FIG. 5b illustrates an electronic model image of a patient's mouth useful for implementing an embodiment of the present invention. The electronic model image for a patient's mouth is typically constructed using two model components, an upper teeth section 104 and a lower teeth section 103. Both of these teeth sections themselves include teeth model elements, gum model elements, and a model base element. The module base element is added to the module when it is generated to aid in the spatial registration of the upper teeth section 104 and the lower teeth 103 section relative to each other as the teeth appear in the patient's mouth. When the location of individual teeth is determined only one of the two teeth sections are processed at any given time.

Figure 6:
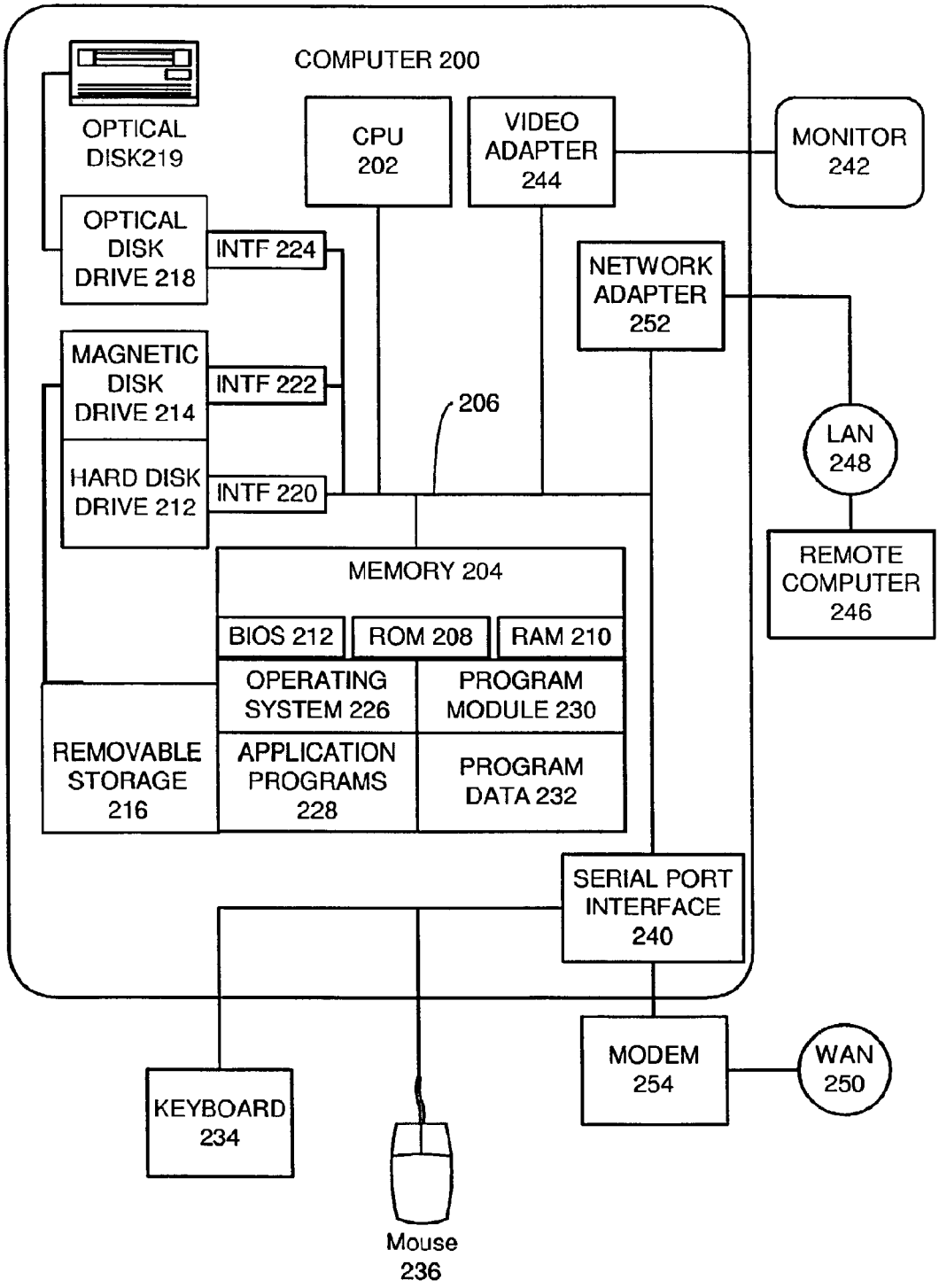
FIG. 6 illustrates an exemplary computing system useful for implementing an embodiment of the present invention.

With reference to FIG. 6, an exemplary system for implementing the invention includes a general-purpose computing device in the form of a conventional personal computer 200, including a processor unit 202, a system memory 204, and a system bus 206 that couples various system components including the system memory 204 to the processor unit 200. The system bus 206 may be any of several types of bus structures including a memory bus or memory controller, a peripheral bus and a local bus using any of a variety of bus architectures. The system memory includes read only memory (ROM) 208 and random access memory (RAM) 210. A basic input/output system 212 (BIOS), which contains basic routines that help transfer information between elements within the personal computer 200, is stored in ROM 208.

The personal computer 200 further includes a hard disk drive 212 for reading from and writing to a hard disk, a magnetic disk drive 214 for reading from or writing to a removable magnetic disk 216, and an optical disk drive 218 for reading from or writing to a removable optical disk 219 such as a CD ROM, DVD, or other optical media. The hard disk drive 212, magnetic disk drive 214, and optical disk drive 218 are connected to the system bus 206 by a hard disk drive interface 220, a magnetic disk drive interface 222, and an optical drive interface 224, respectively. The drives and their associated computer-readable media provide nonvolatile storage of computer readable instructions, data structures, programs, and other data for the personal computer 200.

Although the exemplary environment described herein employs a hard disk, a removable magnetic disk 216, and a removable optical disk 219, other types of computer-readable media capable of storing data can be used in the exemplary system. Examples of these other types of computer-readable mediums that can be used in the exemplary operating environment include magnetic cassettes, flash memory cards, digital video disks, Bernoulli cartridges, random access memories (RAMs), and read only memories (ROMs).

A number of program modules may be stored on the hard disk, magnetic disk 216, optical disk 219, ROM 208 or RAM 210, including an operating system 226, one or more application programs 228, other program modules 230, and program data 232. A user may enter commands and information into the personal computer 200 through input devices such as a keyboard 234 and mouse 236 or other pointing device. Examples of other input devices may include a microphone, joystick, game pad, satellite dish, and scanner. These and other input devices are often connected to the processing unit 202 through a serial port interface 240 that is coupled to the system bus 206. Nevertheless, these input devices also may be connected by other interfaces, such as a parallel port, game port, or a universal serial bus (USB). A monitor 242 or other type of display device is also connected to the system bus 206 via an interface, such as a video adapter 244. In addition to the monitor 242, personal computers typically include other peripheral out put devices (not shown), such as speakers and printers.

The personal computer 200 may operate in a networked environment using logical connections to one or more remote computers, such as a remote computer 246. The remote computer 246 may be another personal computer, a server, a router, a network PC, a peer device or other common network node, and typically includes many or all of the elements described above relative to the personal computer 200. The network connections include a local area network (LAN) 248 and a wide area network (WAN) 250. Such networking environments are commonplace in offices, enterprise-wide computer networks, intranets, and the Internet.

When used in a LAN networking environment, the personal computer 200 is connected to the local network 248 through a network interface or adapter 252. When used in a WAN networking environment, the personal computer 200 typically includes a modem 254 or other means for establishing communications over the wide area network 250, such as the Internet. The modem 254, which may be internal or external, is connected to the system bus 206 via the serial port interface 240. In a networked environment, program modules depicted relative to the personal computer 200, or portions thereof, may be stored in the remote memory storage device. It will be appreciated that the network connections shown are exemplary, and other means of establishing a communications link between the computers may be used.

Additionally, the embodiments described herein are implemented as logical operations performed by a computer. The logical operations of these various embodiments of the present invention are implemented (1) as a sequence of computer implemented steps or program modules running on a computing system and/or (2) as interconnected machine modules or hardware logic within the computing system. The implementation is a matter of choice dependent on the performance requirements of the computing system implementing the invention. Accordingly, the logical operations making up the embodiments of the invention described herein can be variously referred to as operations, steps, or modules.

Figure 7A:
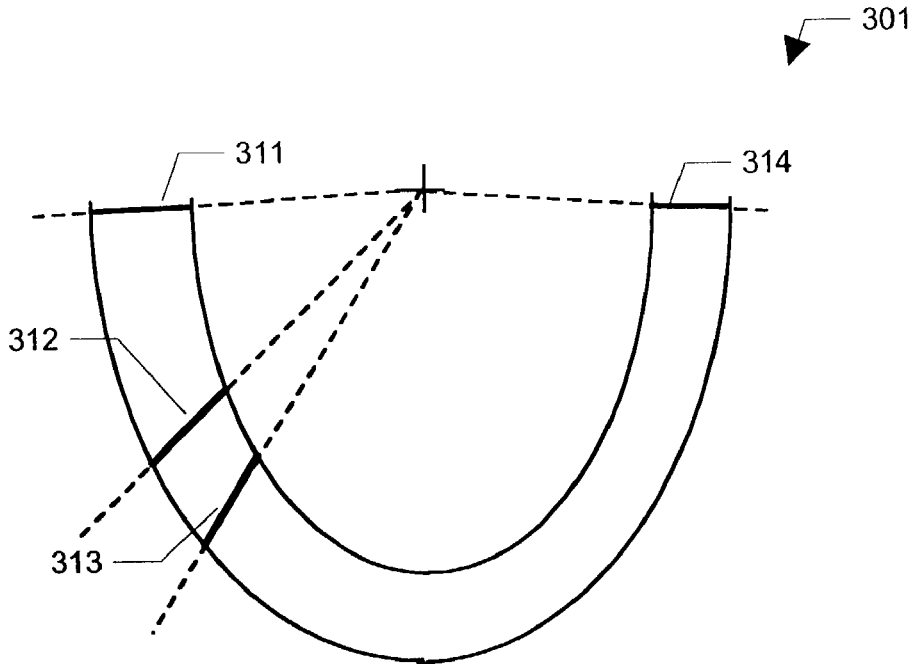
FIGS. 7a-b illustrate horizontal processing elements determined from the electronic model image to identify locations of individual teeth according to an embodiment of the present invention.
Figure 7B:
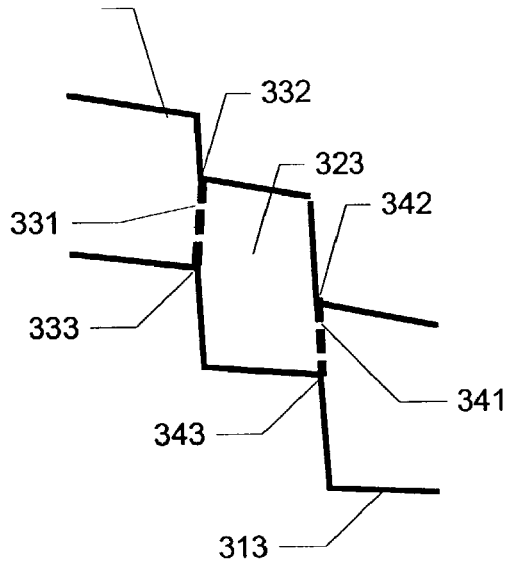

FIG. 7a-b illustrate horizontal processing elements determined from the electronic model image to identify locations of individual teeth according to an embodiment of the present invention. In order to identify the locations of individual teeth, horizontal processing of the electronic model image may occur. First, a horizontal plane is determined through the middle of the electronic model image. This horizontal plane is at a location between the highest most point of the image, which would represent a point on a crown of a tooth, and the model base element which has been added to the impression of the teeth. The resultant 2D image of the electronic model is shown in FIG. 7a. The model of the teeth 301 generally follow an elliptical curve that rotates about a center point. The model is typically bound at either end 311,314 at points corresponding to the edge of the back two teeth, 311, 314. The separation of teeth in the middle of the model are specified using cut lines 312 and 313 located on either side of a tooth 315. The separation of these two cut lines 312 313 is known to be a distance greater than a minimum horizontal separation distance.

This minimum horizontal separation distance may be a fixed minimum number for all patients as all teeth are expected to be greater than some minimum size. This minimum horizontal separation distance may also be a specified minimum size based upon the known size of the patient's mouth. This variation will account for scaling of minimum tooth sizes based upon the general idea that individual patient's with larger mouths will generally possess larger teeth. Additionally, the minimum horizontal separation distance may also be determined by using knowledge of the type of teeth known to exist in various portions of the mouth. For example, teeth that are expected to be located between back edge 311 and cut line 312 would typically be molars. Teeth expected in the center of the model would typically be incisors. These types of teeth are known to possess different sizes and shapes; as such, these known differences may be used to vary the minimum horizontal separation distance when determining cut lines between teeth.

FIG. 7b illustrates a small segment of the horizontal plane cut through the electronic model image. In this subset image, the model consists of an inner image surface 321 and an outer image surface 313. An individual tooth 323 may be identified using a left cut line 331 and a right line 341. The left cut line 331 may be specified by locating two end points 332 and 333 in which the distance between the inner image surface 321 and the outer image surface 322 are locally minimum distances. In some cases, a horizontal plane may be cut at a location in which a individual tooth is not near or touching another tooth. When this occurs these local minimum distances will be zero. When teeth are close or touching each other, the cut lines are needed to segment the teeth into separate elements in the electronic model image.

The process of looking for these locally minimum distances may be performed at several horizontal height locations between the model base element and the tooth peaks. By finding cut lines at various horizontal locations, separation planes between the teeth may be specified. These various cuts should be made a locations that are centered upon the known spacing between the model base element and the peak of the teeth. If the horizontal cut is made close to the model base element, many teeth may be located so close together that accurate separation of the teeth may not be possible. If the horizontal cut is made too close to the peak of the teeth, features of the crowns of the teeth may be mistaken for separation between the teeth.

Figure 8A:
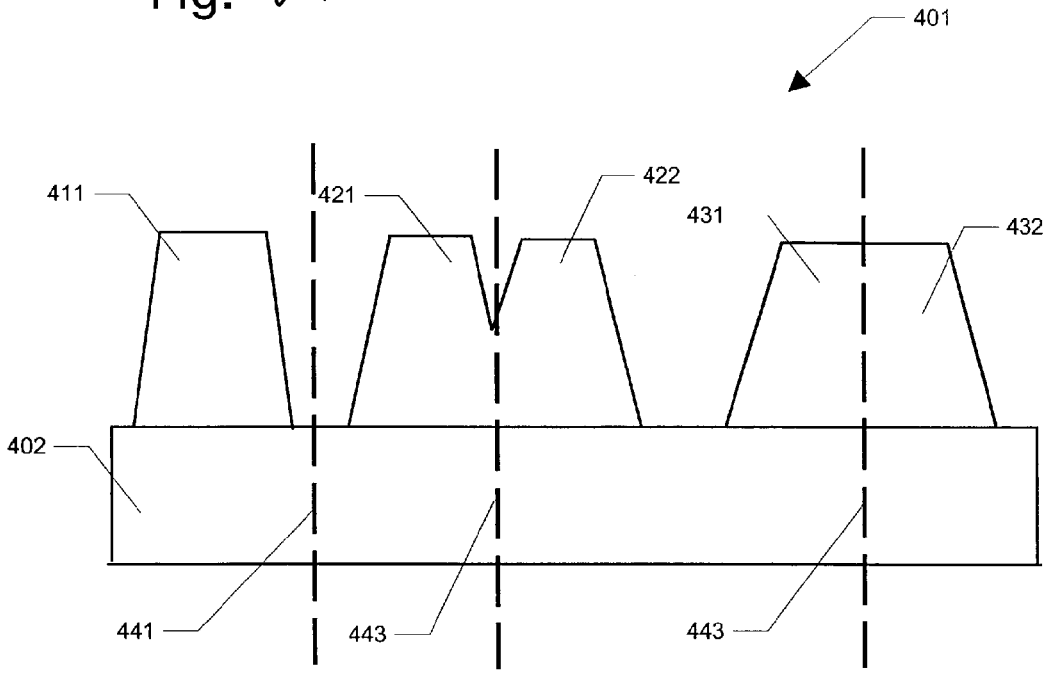
FIGS. 8a-b illustrate vertical processing elements determined from the electronic model image to identify locations of individual teeth according to an embodiment of the present invention.
Figure 8B:
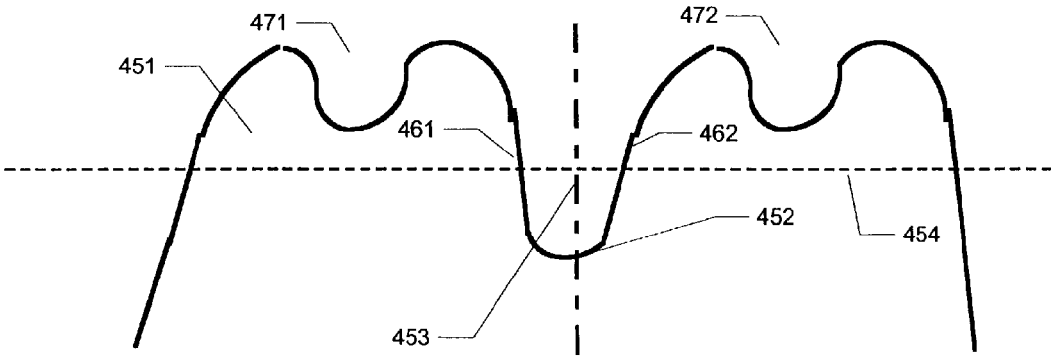

FIGS. 8a-b illustrate vertical processing elements determined from the electronic model image to identify locations of individual teeth according to an embodiment of the present invention. Similar to the horizontal processing, vertical analysis of the model data may that is viewed along a vertical cut made through an elliptical arc through the module may also permit the automatic determination of teeth separation cut lines. FIG. 8a illustrates a sequence of teeth having various relation ships to neighboring teeth. Tooth 411, which is located on model base element 402, is shown to be completely separate from its neighboring tooth 421. In such a situation, cut line 441 between tooth 411 and tooth 421 may be easily determined by locating the local minimum 452 for a vertical location along an upper surface of the model between tooth 421 and 422. This situation is shown in more detail in FIG. 4b where cut line 453 is made at the local minimum 452 between tooth 451 and tooth 452. In this first situation, the local minimum 452 is easily recognized as a cut line as the local minimum is located at the patient's gums and as such is located close to the model base element 402.

A similar situation may arise in determining cut line 443 between tooth 421 and tooth 422. In this situation, the two teeth are closer together. As a result, the two teeth touch each other at a point mid way between the teeth peaks and the gum line. When this situation is compared to cut line 441, the same results shown in FIG. 8b occur. The only difference between these situations is that the location of the local minimum 452 will be higher than the prior case but may still be recognized if the local minimum is below threshold 454.

A third possible situation may arise as is illustrated by cut line 443 located between tooth 431 and tooth 432. In this situation, no discernable separation between the two teeth are seen as they are completely overlapping each other. This situation occurs when the local minimum between two teeth 453 is located above a threshold 454 such that it cannot be distinguished between local features of the teeth crowns 471-472. In this situation, the cut line 443 may be determined less accurately by determining a point estimated to be between tooth 431 and 432.

If a system combines the cut lines determined using both the horizontal element processing shown in FIG. 7 and the vertical processing shown in FIG. 8, all of the cut lines between teeth in an electronic model image may be determined. When the horizontal element processing and the vertical element processing find cut lines that are identical, the cut line is know to be correct with a high degree of certainty. When a high level of confidence may be given to a cut line from either horizontal or vertical processing but not both, an accurate cut line may still be determined with a degree of certainty. Only when both horizontal and vertical processing cannot determine a location of a cut line with a high level of confidence must additional information be considered.

Once many of the locations of teeth are determined using just the vertical and horizontal processing described above, the locations of other teeth may be estimated using additional information. For example, if the number of teeth known to be present is considered, the number of teeth not found using the above process may be determined. The locations of the known teeth may suggest regions where no known teeth were found. Using these additional pieces of information may allow the remaining possible cut lines found in the horizontal and vertical processing to be ranked to locate the most likely location in a region where teeth were not found to propose the most likely remaining cut line locations.

Figure 9:
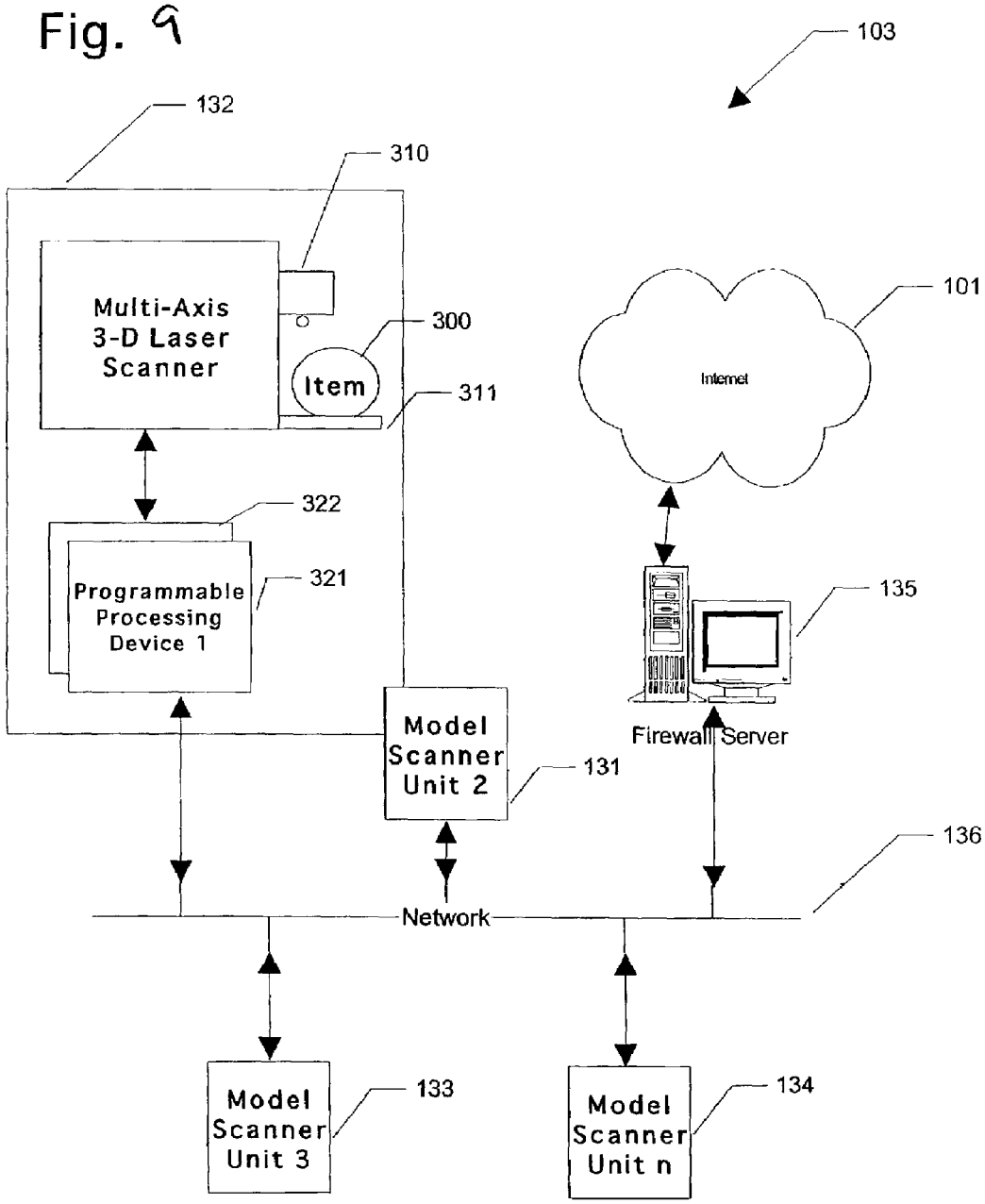
FIG. 9 illustrates a distributed computing system for the creation and distribution of electronic models of objects according to one embodiment of the present invention.

FIG. 9 illustrates a distributed computing system for the creation and distribution of electronic model images of objects according to one embodiment of the present invention. End users operate a plurality of different computing systems 110-113 to perform their respective computing tasks. End users typically use one general purpose computing system for a variety of tasks. In order for use of imaging systems to replace paper and model based systems, the imaging system used by end users 110-113 consist of laptop and desktop computing systems.

These computing systems typically possess a mechanism to communicate with other computing systems over a communications network 101. The Internet 101, as a publicly available communications network, provides an available communications path between virtually any two computing systems after they first connect to the Internet. While other communications mechanisms exist and may be used, the Internet provides a well-known mechanism to communicate data between two computing systems.

In an image-based electronic model image system, an end user 110 communicates over a communications network 101 to a server 121 to retrieve electronic eModels from a database 122. The end user 122 may be located anywhere a connection to the communications network 101 exists to retrieve the eModels from the database 122. This database 122 may be located within an eModel data server system 102 that is maintained by third-parties that provide maintenance, data back-up, and similar data processing overhead functions that are not an overriding concern for an end user. This data back-up, for example, may consist of long-term archiving of data to replace maintenance of physical models that have in the past required a great deal of effort and expense to complete.

The electronic model images themselves consist of a data file stored on the server 121 in a database 122 that allows quick and efficient access for users. These electronic model images are generated in a separate electronic model image generation system 103 that consists of one or more model scanning units 131-134. These units 131-134 are connected together using a local communications network 136 and a communications path 135 to the Internet 101. As such, electronic model images, once generated may be transferred to the electronic model image Data server system 102 for ultimate use by end users 110-113.

Figure 10:
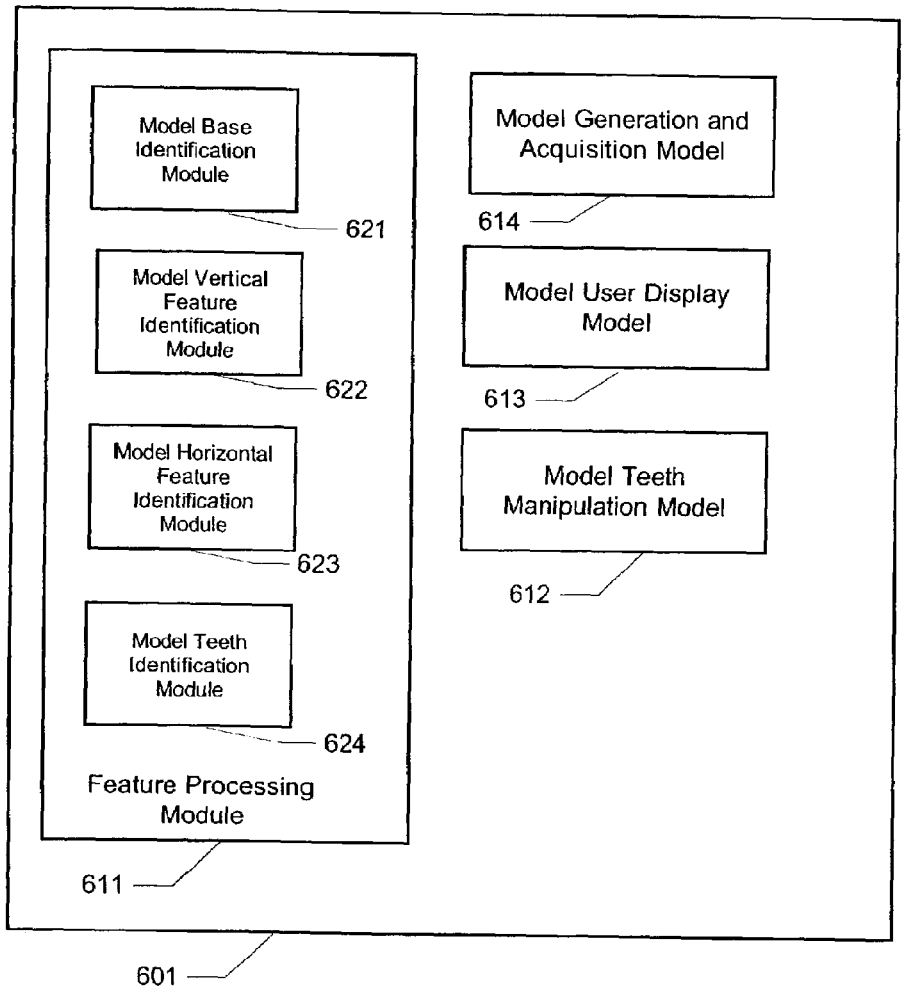
FIG. 10 illustrates a block diagram for an tooth location determination processing system according to an embodiment of the present invention.

FIG. 10 illustrates a block diagram for an tooth location determination processing system according to an embodiment of the present invention. A computer implemented system 601 used to process electronic model images includes several processing modules including a feature processing module 611, a model generation and acquisition module 614, a module user display module 613 and a model teeth manipulation module 612. The feature processing module 611 itself includes a model base identification module 621, a model vertical feature identification module 622, a model horizontal feature identification module 623, and a module teeth identification module 624. The model generation and acquisition module 614 is used to generate and obtain electronic model images from remote storage for use in processing within the system 601. The module user display module 613 outputs the electronic model images onto a computer display device for viewing by a user of the system 601. The model teeth manipulation module 612 is used by an end user of the system to obtain measurements relating to the electronic model as well as manipulate the location of teeth when a proposed treatment plan for a patient is considered as shown in FIG. 5a.

The model base identification module 621 is used to identify the model base element from teeth and gum data elements obtained from within the electronic model image. The model vertical feature identification module 622 performs the processing described above with reference to FIG. 8 in which vertical cut lines are identified. The model horizontal feature identification module 623 performs the processing described above with reference to FIG. 7 in which horizontal cut lines are identified. The module teeth identification module 624 performs the processing described above with reference to FIG. 8 in which vertical and horizontal cut lines are used to identify all of the teeth found within the electronic model image.

Figure 11:
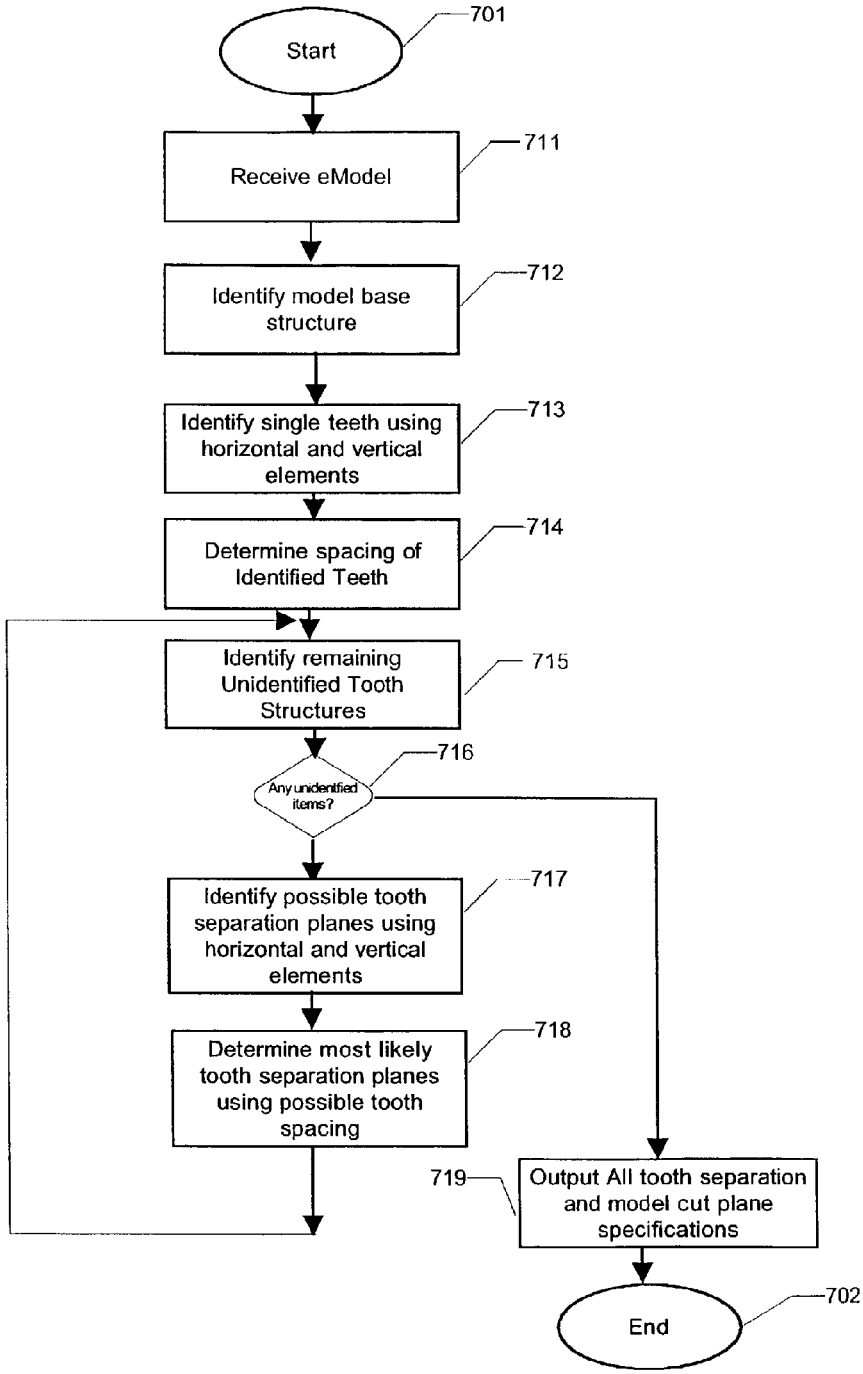
FIG. 11 illustrates an operational flow for determining the locations of teeth within an electronic model image according to yet another example embodiment of the present invention.

FIG. 11 illustrates an operational flow for determining the locations of teeth within an electronic model image according to yet another example embodiment of the present invention.

The processing begins 701 and an electronic model image is obtained for use in the processing in module 711. In this module, the upper teeth section or lower teeth section are selected for separate processing. Once an appropriate teeth section is selected, module 712 identifies the model base element for use in generating vertical and horizontal cut lines.

Module 713 generates the horizontal and vertical cut lines and identifies single teeth that are known to be identified with a high degree of certainty. This high degree of certainty is known when either of a particular vertical cut line or a particular vertical cut line has been identified with a high level of confidence. This level of confidence may relate to a local minimum distance between horizontal cut lines being less than a specified value. Similarly, this level of confidence may relate to the local minimum used to define a vertical cut line being below a specified threshold. When the cut lines on both sides of a tooth are known to a high level of certainty, the tooth may be confidently identified.

Once some of the teeth are identified, module 714 determines the number and spacing of the known teeth. This spacing of the teeth may identify errors if teeth are found to be overlapping in location or are found to be less than a minimum size. This spacing may also be used to identify regions of the electronic model image where teeth have yet to be found.

These regions containing possible unidentified teeth are then searched in module 715 to identify the know vertical and horizontal structures that may represent addition cut lines. Using these identified structures, the most likely regions where the number of unidentified teeth may be found. Test module 716 determines if additional teeth need to be found. If not, module 719 outputs the specification of all found teeth and the electronic model cut planes that may be used to separate the module into a set of separate teeth images before the processing ends 702.

If test module 716 determines that additional teeth need to be identified, module 717 identifies possible tooth separation planes in likely regions where teeth have not still been found using the previously identified possible vertical and horizontal cut lines. The possible separation planes are ranked to find the most likely candidate in module 718. This candidate is used to identify a tooth before the regions of unidentified teeth are updated for use in further processing. Once a tooth is identified, the processing returns to test module 715 in an attempt to find additional teeth. The processing within this loop continues until all of the teeth are found.

FIG. 6 illustrates an example of a suitable operating environment 121 in which the invention may be implemented. The operating environment is only one example of a suitable operating environment 121 and is not intended to suggest any limitation as to the scope of use or functionality of the invention. Other well known computing systems, environments, and/or configurations that may be suitable for use with the invention include, but are not limited to, personal computers, server computers, held-held or laptop devices, multiprocessor systems, microprocessor-based systems, programmable consumer electronics, network PCs, minicomputers, mainframe computers, distributed computing environments that include any of the above systems or devices, and the like.

The invention may also be described in the general context of computer-executable instructions, such as program modules, executed by one or more computers or other devices. Generally, program modules include routines, programs, objects, components, data structures, etc. that perform particular tasks or implement particular abstract data types. Typically the functionality of the program modules may be combined or distributed in desired in various embodiments.

A network server 121 typically includes at least some form of computer readable media. Computer readable media can be any available media that can be accessed by the network server 110. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, BC-ROM, digital versatile disks (DVD) or other optical storage, magnetic cassettes, magnetic tape, magnetic disk storage or other magnetic storage devices, or any other medium which can be used to store the desired information and which can be accessed by the network server 110.

Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

The foregoing description of the exemplary embodiments of the invention has been presented for the purposes of illustration and description. They are not intended to be exhaustive or to limit the invention to the precise forms disclosed. Many modifications and variations are possible in light of the above teaching. It is intended that the scope of the invention be limited not with this detailed description, but rather by the claims appended hereto.

What is claimed is:

1. A computer implemented method of automatic marking of locations on a cast for creation of an indirect bonding tray, the method comprising:

displaying an electronic model image corresponding to a cast of a patient, the cast including individual teeth of the patient in start positions;

storing an array of start coordinates for the individual teeth;

storing an array of finish coordinates when the teeth have been moved to finish positions;

storing an array of bracket mark locations for one or more of the individual teeth with respect to the finish positions; and calculating the bracket mark locations in connection with the start positions based on the stored start and finish coordinates, wherein calculating the bracket mark locations in connection with the start positions includes transforming the bracket mark locations with respect to the finish positions with an inverse matrix, the inverse matrix being generated based on the stored start coordinates and finish coordinates for the individual teeth, and wherein the bracket mark locations can be viewed with the teeth in the start positions.

2. The method of claim 1, further comprising generating an output file including the bracket mark locations in connection with the start positions and transmitting the output file to a marking device configured to mark a cast of the teeth of the patient directly to indicate the bracket mark locations in connection with the start positions.

3. The method of claim 1, further comprising manually cutting the electronic model image into individual teeth.

4. The method of claim 1, further comprising automatically cutting the electronic image into individual teeth.

5. The method of claim 4, comprising:

determining possible vertical cut lines within a vertical plane cut through the electronic model image corresponding to possible separation lines between teeth; and automatically determining locations of individual teeth using the possible vertical cut lines.

6. A system for marking locations on a cast for creation of an indirect bonding tray, the system comprising:

means for displaying an electronic model image corresponding to a cast of a patient with individual teeth in start positions;

means for storing an array of start coordinates for the individual teeth;

means for storing an array of finish coordinates when the individual teeth are moved to finish positions;

means for storing an array of bracket mark locations for one or more of the individual teeth with respect to the finish positions; and means for calculating bracket mark locations in connection with the start positions based on the stored start and finish coordinates, wherein calculating the bracket mark locations in connection with the start positions includes transforming the bracket mark locations with respect to the finish positions with an inverse matrix, the inverse matrix being generated based on the stored start coordinates and finish coordinates for the individual teeth, and wherein the bracket mark locations can be viewed with the individual teeth in the start positions.

7. The system of claim 6, further comprising:

means for generating an output file with the bracket mark locations in connection with the start positions; and means for transmitting the output file to a marking device for directly marking a cast with the bracket mark locations.

8. The system of claim 6, further comprising the means for manually cutting the electronic model image into individual teeth.

9. The system of claim 6, further comprising means for automatically cutting the electronic image into individual teeth.

10. The system of claim 9, comprising:

means for determining possible vertical cut lines within a vertical plane cut through the electronic model image corresponding to possible separation lines between individual teeth; and means for automatically determining locations of individual teeth using the possible vertical cut lines.

11. A system for marking of locations on a cast for creation of an indirect bonding tray, the apparatus comprising:

a) a video display unit, the video display unit arranged and configured to display electronic model images;

b) a plurality of memory locations;

c) an input device for accepting input data from a user and for transmitting the input data; and d) a processor operatively connected to the video display unit, the memory locations, and the input device, the processor arranged and configured to accept the transmitted input data, to process data, and to store and retrieve data from the memory locations, wherein the processor:

i) determines an array of start coordinates for individual teeth and stores the start coordinate array in the memory locations;

ii) determines an array of finish coordinates for individual teeth, subsequent to the individual teeth being moved to finish locations via the input device, and stores the finish coordinate array in the memory locations;

iii) stores an array of bracket mark locations in the memory locations, the bracket mark locations provided by input data from the input device when the individual teeth are in the finish locations; and iv) calculates the bracket mark locations in connection with the start locations based on the stored start and finish coordinate arrays, wherein calculating the bracket mark locations in connection with the start positions includes transforming the bracket mark locations with respect to the finish positions with an inverse matrix, the inverse matrix being generated based on the stored start coordinates and finish coordinates for the individual teeth, and wherein the bracket mark locations can be viewed with the individual teeth in the start locations.

12. The system of claim 11, further comprising a marking device for transferring the stored bracket mark locations to a study cast.

13. The system of claim 12, wherein the marking device includes a robotic arm.

14. The system of claim 12, wherein the marking device includes a pen.

* * * * *